United States Patent [19]

Christenson, II

[11] Patent Number: 4,944,940

[45] Date of Patent: Jul. 31, 1990

[54] BUCK LURE

[76] Inventor: Leland G. Christenson, II, Rt. 1, Box 27, Eleva, Wis. 54738

[21] Appl. No.: 258,076

[22] Filed: Oct. 13, 1988

Related U.S. Application Data

[63] Continuation of Ser. No. 92,160, Sep. 2, 1987, abandoned.

[51] Int. Cl.$^5$ ............................................ A01N 25/00
[52] U.S. Cl. ......................................................... 424/84
[58] Field of Search ........................................... 424/84

[56] References Cited

U.S. PATENT DOCUMENTS

| | | | |
|---|---|---|---|
| 2,959,354 | 11/1960 | Beck | 424/84 |
| 3,046,192 | 7/1962 | Bilyeu | 424/84 |
| 3,119,650 | 1/1964 | Bilyeu | 21/117 |
| 4,302,899 | 12/1981 | DeHart | 43/1 |
| 4,667,430 | 5/1987 | Ziese, Jr. | 43/1 |

OTHER PUBLICATIONS

Portions of magazine entitled *The Deer Trail*, Spring 1987, vol. 4, Issue 2.
Portions of magazine entitled *Deer & Deer Hunting*, Jun. 1987.

*Primary Examiner*—Douglas W. Robinson
*Assistant Examiner*—Joseph A. Lipovsky
*Attorney, Agent, or Firm*—Andrus, Sceales, Starke & Sawall

[57] ABSTRACT

The present disclosure relates to a buck lure comprising a deer tarsal gland and a fluid in which the predominant ingredient is deer urine. Other ingredients include essence of deer interdigital gland, essence of deer femoral gland and a preservative.

29 Claims, No Drawings

BUCK LURE

This application is a continuation, of application Ser. No. 092,160, filed Sept. 2, 1987 now abandoned.

Background of the Invention

1. Field of the Invention

The present invention is generally directed to a buck lure, and specifically to a buck lure which distinguishes dominant mature bucks from younger bucks, does and fawns.

2. Description of the Prior Art

Hunting wild animals, and especially deer, is an art requiring the proper mix of intelligence, patience, endurance and the right equipment. Because deer rely heavily on their highly developed sense of smell to alert them to a multitude of factors, such as danger, food, the presence of other animals, it is necessary for the hunter to blend into the environment, without alerting the deer to his presence. It is also very helpful to provide some means to attract the animal to the hunter's vicinity.

With respect to deer, and especially the male of the species or the buck, a buck lure is often used to tempt the buck. Buck lures have application not only for deer hunters, but for photographers and other wildlife enthusiasts.

The ideal time for hunting bucks, and especially the mature or dominant bucks, is during the time that does are in heat or estrus and are sexually receptive. During this time, bucks tend to become very predictable in their pattern of activity. The mating season puts bucks in a state of sexual excitement called a "rut". During rut season, a buck will mark off his "breeding territory". The buck will then attempt to prevent other bucks from entering his breeding territory, and will herd up the available does in heat for breeding.

One method of marking a buck's breeding territory is by the use of a "mating scrape", which is generally a circular area on the ground about two to three feet in diameter that has been cleared of all leaves and debris by the buck pawing or scraping the area with his hooves. After the scrape has been made, the buck marks the scrape by urinating down along the tarsal gland on his leg. The tarsal gland is a communicative gland located on the hock of a deer leg. It is used to communicate to other deer when a buck enters the rut stage. The tarsal gland contains both sebaceous and sudorific glands connected to hair follicles that act as ducts to bring pheromone secretions to the surface. These secretions form a musky-type of dust on the hair follicles in the area of the tarsal gland.

The mixture of the musk from the tarsal gland and the urine then flows over the femoral gland, located between the tarsal gland and the hoof, and the interdigital gland, located on the hoof of the deer. A mixture of the urine and the three glands is then deposited on the ground which produces the rutting odor signaling the buck's mating scrape.

The scrape is thus a visual signal for both does and bucks. After sensing the scrape, does will generally enter the area of the scrape and urinate on it to also signal their presence and their time of heat. Other bucks, who come into the area of the mating scrape, sense that there is a dominant buck, i.e., a buck who has marked off the area as his breeding ground, and acknowledge the scrape as either a warning or a challenge of another buck's presence.

An effective strategy for hunters is to hunt in an area of an active mating scrape. Alternatively, a "mock scrape" can be made by imitating the buck's actions. An area is cleared in an appropriate location and a commercially obtained lure containing the required scent is placed at or near the scrape.

The predominant type of deer lure used today is in the form of a liquid which is generally prepared by fermenting tarsal glands of several deer in urine. The urine is usually a combination of buck, doe and fawn urine. The tarsal glands, which are used in this liquid deer lure, are also generally a combination of buck, doe and fawn tarsal glands. A preservative or diluting agent is usually also added. The fluid scent may simply be applied to a tree or scrape area, or the scent may be dispelled by placing the fluid in specially formed containers for dispensing the aromatic scent. Examples of such containers may be found in U.S. Pat. Nos. 2,959,354 to Beck, 4,302,899 to DeHart, 3,119,650 and 3,046,192 to Bilyeu, and 4,667,430 to Ziese, Jr.

The problem with the lures of the prior art, is that they will emit an odor common to a deer park. Thus, a buck entering the area of the lure is led to believe that there is a herd of deer, including all forms and ages of bucks, does and fawns. Because younger deer are naturally gregarious, the deer lure of the prior art tends to attract only deer of this type. However, a dominant buck, generally a more mature trophy buck, is primarily a solitary animal. During the summer, he roams in bachelor groups, only separating in the fall to set up his individual breeding territory. Then, the dominant bucks duel among themselves to establish a hierarchy. The strongest and most dominant buck in the area will set up a scrape line, i.e., an area marked off by scrapes, leaving the other bucks to find less desirable areas. The buck will then monitor these scrapes for signs of does. When a doe enters a scrape area and shows signs of heat, the buck enters his rutting stage. He will then keep track of the does coming into heat and protect his breeding area from other bucks. If a dominant buck senses that another buck is in his breeding area, he will vigorously defend the breeding area by tracking down the intruder bucks and forcing them off his breeding area.

In order to force the buck into the open, it is then necessary to provide some type of lure, whether it be a less dominant buck or an artifical lure which will alert the dominant buck of an interloper on his breeding ground.

Summary of the Invention

It is therefore an object of the present invention to overcome the problems of prior art buck lure scents.

It is another object of the present invention to provide a deer lure scent which will overcome the problem of prior art deer lures which mimic deer park situations.

It is another object of the invention to prepare a buck lure which will provide the dominant buck with the sensory illusion that a strange buck has entered the dominant buck's breeding territory.

It is another object of the invention to provide a lure which will mimic a single buck rutting scent.

It is further an object of the present invention to provide a deer lure which has the strong rutting odor of an individual buck that dominant bucks will actively seek out in order to protect their breeding territory.

These objects and others are provided for by the present invention which is directed to a deer lure kit comprising a substantially intact deer tarsal gland and a deer scent solution which includes deer urine, wherein the deer scent solution is adapted to admix with the tarsal gland in order to produce a deer attracting scent. The tarsal gland may be either a fresh tarsal gland recently taken from a deer or a dried, preferably freeze-dried, tarsal gland. The deer scent solution will preferably further include an essence of a buck's interdigital gland and femoral gland, as well as a preservative.

The present invention is more particularly directed to a buck lure kit comprising a substantially intact buck tarsal gland and a solution comprising buck urine which has been fermented with femoral glands and interdigital glands.

The present invention is also directed to a method of attracting deer with a deer lure which is comprised of a substantially intact deer tarsal gland and deer scent solution including deer urine, which has been fermented with interdigital glands and femoral glands, wherein the steps include mixing the solution with the tarsal gland for a period of from approximately a few minutes to a few days, and placing the deer lure in an environment inhabited by deer. Thus, the present invention is unique in that it mimics the scent of a single deer rather than a deer herd.

Although it is within the scope of the present invention to provide a lure using a doe tarsal gland, which mimics a single doe smell for the purposes of attracting bucks, the buck lure of the present invention is more specifically directed to a buck lure which mimics the scent of a single buck in the rutting stage. A dominant buck will smell this lure and think that another buck has entered his breeding territory to challenge his dominance and breed his does.

The lure is thus intended to specifically single out big, trophy bucks by providing a scent which combines the tarsal gland from an individual buck with the femoral gland, the interdigital gland and buck urine. As the dominant buck monitors his scrape line to see if any other bucks or does have come into his area, he will smell the scent eminating from the buck lure of the present invention and think that another buck has entered his territory to challenge him. The dominant buck will then come to the scrape in which the buck lure is located and urinate down across his tarsal gland and along the other leg glands, leaving a signal that the dominant buck is asserting his dominance in the area.

Thus, the buck lure of the present invention advantageously will cause a buck to lower his defenses in favor of protecting his territory. In other words, it will bring the buck out into the open for prolonged visual contact by the hunter.

These and other advantages of the present invention will now be more specifically detailed in the following disclosure:

Detailed Disclosure of the Invention

The present invention is specifically directed to the deer scent odor which is emitted from the chemical interaction of the deer urine with the tarsal gland, which produces a rutting odor that a buck perceives as a territorial infringement or a challenge. It is also within the scope of the invention to provide a deer lure comprising a doe tarsal gland and doe urine which will give the buck the impression that a doe has entered his breeding territory.

The key element of the buck lure of the present invention is the tarsal gland. This gland has been described before as a gland on the hock of a buck which produces a musky odor. When mixed with urine, the combination of the urine and tarsal gland signifies that a buck is in the area. As interpreted in the present invention, the tarsal gland used in the buck lure is a substantially intact gland which has been removed from the hide of deers, generally during the deer hide processing or tanning stage. It is within the scope of the present invention to utilize only so much of the tarsal gland as is necessary to produce an effective buck lure. Thus, only a portion of the tarsal gland may be necessary for each buck lure kit. For example, a tarsal gland of a mature animal is generally large enough to accomodate two buck lure kits. Therefore, the tarsal gland may be cut in half and utilized for two kits.

It is within the scope of the present invention to utilize a fresh tarsal gland in the kit. However, for convenience sake and for long-term storage, the tarsal gland is preferably dried.

The tarsal gland may be prepared as follows: The glands are cut off a deer hide, generally prior to the time the hide is cured. The glands are then trimmed to remove any excess skin and put through a double-rolled rolling press in order to remove excess liquid from the hide. Following the rolling press, the gland is perforated by coacting spiked rollers which aid in the additional removal of excess water from the tissue in the back of the gland. The gland is then again placed through a rolling press.

If the tarsal gland is not to be used immediately, it is preferably dried, either naturally, by convection heating or by freeze-drying.

Freeze-drying is preferred because it is quicker and freezes the gland into desired shapes. Freeze-drying methods are known to the art. Basically, the gland is placed in a freeze-dryer, which drys the moisture out of the gland by freezing it solid. A vacuum pump then removes the liquid from the freeze-dryer. The dried product remains somewhat pliable.

The gland is then cut into desired shape and size.

It is within the scope and indeed a preferred embodiment to include at least the essence of two other deer glands: (1) the interdigital gland and (2) the femoral gland. As explained previously, both of these glands are located on the hind leg of a deer beneath the tarsal gland and in the track of the urine flow to the ground. Thus, the distinct rutting odor which alerts the buck to the presence of another buck would include scents derived from these other two glands. Rather than to use these two glands intact, it is preferred to soak the glands either in the urine solution or in a preservative solution prior to adding the urine. This procedure will put the gland scent in the fluid which is to be added to the tarsal gland.

Turning now to the fluid, the main ingredient is deer urine. If a buck tarsal gland is used in the buck lure kit, then buck urine should be used full strength in order to provide continuity between the gland and urine. Although it would be preferred to utilize the urine from an individual buck, practicality dictates that the urine of different bucks can be combined. Buck urine may be obtained by methods known to the art, such as collecting the urine from caged bucks in a deer park.

It is also preferred to add a preservative to the buck solution. Useful preservatives include glycerine, propylene glycol, mineral oil, and alcohols.

The fluid solution is prepared as follows: a minimum quantity of femoral and interdigital glands to place the gland scent in the fluid is emulsified in the preservative.

The preservative solution is then allowed a sufficient time to ferment, generally about three months. This time may be shortened if the solution is agitated. Approximately one part of the preservative mixture is then mixed with approximately three parts of urine in order to create the buck lure fluid. Optionally, the fluid can be strengthened by adding more musk from additional tarsal glands. The purpose of this fluid is to mimic the natural body fluids of the deer.

For convenience, a ring is attached to the tarsal gland to enable the gland to be hung above a scrape area. It is preferable to have the ring made of plastic or some other neutral material, as metal may oxidize when contacted with water. The oxidized odor would then be picked up by the buck, alerting him to some danger. It is preferred that the ring be attached on the musk side of the tarsal gland. As the hair on the gland flows in one direction, the ring should be hung on the downside of the hair flow so that when the gland is hung up, the solution would flow down into the hair folicle toward the skin. Thus, the tarsal gland would retain the scent longer.

Although there are a number of ways to package the buck lure kit, it is preferred to place the tarsal gland in a plastic bag which may be sealed shut, such as a bag having a tie-wrap or an interlocking mechanism. The solution is kept separate, preferably in a glass bottle as the urine in the solution may tend to mix with the polymers in a plastic bottle and contaminate the solution.

When the buck lure is ready to be used, the tarsal gland is rehydrated by adding a sufficient quantity of the solution to the gland in the plastic bag and allowing the tarsal gland to rehydrate. This period may take anywhere from a few minutes to 12 hours.

After the tarsal gland has been sufficiently rehydrated, the gland is preferably hung approximately two feet off the ground and up wind of where a buck might be expected to cross. As indicated previously, the lure may be used at a mock or a real scrape. Alternatively, the buck lure can be tied to a string and dragged on the ground in order to simulate a deer trail.

It is understood that the invention is not confined to the particular construction and arrangement herein described but embraces such modified forms thereof as comes within the scope of the following claims.

What is claimed is:

1. A buck lure kit comprising:
   (a) substantially intact deer tarsal gland from one deer; and
   (b) a deer scent fluid including deer urine, wherein the deer scent fluid is adapted to admix with the tarsal gland to produce a deer attracting scent.

2. The kit according to claim 1 wherein the tarsal gland is a fresh tarsal gland.

3. The kit according to claim 1 wherein the tarsal gland is a dried tarsal gland.

4. The kit according to claim 3 wherein the tarsal gland is freeze-dried.

5. The kit according to claim 1 wherein the tarsal gland is a doe tarsal gland and the urine is doe urine.

6. The kit according to claim 1 wherein the tarsal gland is a buck tarsal gland and the urine is buck urine.

7. The kit according to claim 1 wherein the deer scent fluid has been previously mixed with deer interdigital glands in order to give the deer scent solution an interdigital gland essence.

8. The kit according to claim 1 wherein the deer scent fluid has been previously mixed with deer femoral glands in order to give the deer scent solution a femoral gland essence.

9. The kit according to claim 1 wherein the deer scent fluid further comprises a preservative selected from the group consisting of glycerine, propylene glycol, mineral oil and alcohol.

10. The kit according to claim 1 wherein the deer scent fluid has been previously mixed with deer interdigital glands and deer femoral glands and a preservative.

11. The kit according to claim 9 wherein the deer scent fluid has the following composition:
    (a) three parts urine; and
    (b) one part preservative.

12. The kit according to claim 11 wherein the preservative has been previously admixed with deer interdigital glands and deer femoral glands.

13. The kit according to claim 12 wherein the deer scent fluid is prepared by:
    (a) fermenting deer interdigital glands and deer femoral glands in a preservative for a sufficient time to give the preservative the required essence of interdigital gland and femoral gland; and
    (b) adding one part of the fluid of step (a) to three parts deer urine.

14. The deer kit according to claim 13 wherein the fluid of step (a) is fermented for approximately three months.

15. The kit according to claim 1 wherein a ring is attached to the tarsal gland.

16. The kit according to claim 15 wherein the ring is attached to the tarsal gland on the downside of the hair flow of the gland.

17. The kit according to claim 15 wherein the ring is comprised of plastic.

18. A process for preparing a buck lure kit comprising:
    (a) excising a tarsal gland from one deer;
    (b) preparing a deer scent fluid comprising deer urine; and
    (c) packaging a substantial amount of the excised tarsal gland and the deer scent fluid separately.

19. The process according to claim 18 further comprising drying the tarsal gland.

20. The process according to claim 19 wherein the process for drying the tarsal gland includes:
    (a) removing a substantial amount of the natural liquid from the excised tarsal gland;
    (b) perforating the tarsal gland to remove excess natural liquid from the tarsal gland; and
    (c) placing the perforated tarsal gland through a rolling press in order to remove further natural liquid.

21. The process according to claim 18 wherein the tarsal gland is freeze-dried.

22. The process according to claim 18 wherein the tarsal gland is a doe tarsal gland and the urine is doe urine.

23. The process according to claim 18 wherein the tarsal gland is a buck tarsal gland and the urine is buck urine.

24. The process according to claim 18 wherein the deer scent fluid has been previously mixed with deer interdigital glands and deer femoral glands and an effective amount of a preservative.

25. A process for preparing a buck lure comprising:
    (a) excising a tarsal gland from the hide of one deer;
    (b) preparing a deer scent fluid comprising deer urine; and (c) adding a sufficient quantity of the deer scent fluid to the tarsal gland to produce a deer attracting scent.

26. The process according to claim 25 wherein the tarsal gland is dried.

27. The process according to claim 26 wherein the tarsal gland is freeze-dried.

28. The process according to claim 26 wherein the deer scent fluid has been previously mixed with deer interdigital glands and deer femoral glands and an effective amount of a preservative.

29. A buck lure comprising a substantially intact deer tarsal gland to which a deer scent fluid has been applied, the deer scent fluid comprising deer urine.

* * * * *